(12) United States Patent
Ryu et al.

(10) Patent No.: US 9,095,264 B2
(45) Date of Patent: Aug. 4, 2015

(54) METHOD AND SYSTEM FOR IDENTIFYING CARDIAC ARRHYTHMIA DRIVER SITES

(71) Applicants: Kyungmoo Ryu, Palmdale, CA (US); Valtino X. Afonso, Oakdale, MN (US)

(72) Inventors: Kyungmoo Ryu, Palmdale, CA (US); Valtino X. Afonso, Oakdale, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

(21) Appl. No.: 13/678,764

(22) Filed: Nov. 16, 2012

(65) Prior Publication Data

US 2013/0066221 A1     Mar. 14, 2013

Related U.S. Application Data

(63) Continuation of application No. 12/923,769, filed on Oct. 7, 2010, now Pat. No. 8,340,766.

(51) Int. Cl.
*A61B 5/044*     (2006.01)
*A61B 5/0452*     (2006.01)
*A61B 5/046*     (2006.01)
*A61N 1/362*     (2006.01)

(52) U.S. Cl.
CPC ............... *A61B 5/0452* (2013.01); *A61B 5/046* (2013.01); *A61N 1/3624* (2013.01)

(58) Field of Classification Search
CPC ..... A61B 5/0452; A61B 5/046; A61N 1/3624
USPC .......................................................... 600/523
See application file for complete search history.

(56) References Cited

U.S. PATENT DOCUMENTS 5,687,737 A     11/1997   Branham et al.
6,023,638 A     2/2000    Swanson
(Continued)

FOREIGN PATENT DOCUMENTS

WO     2007/137077     11/2007
WO     2010/054409     5/2010
WO     2004/050179     6/2014

OTHER PUBLICATIONS

"International Search Report and Written Opinion", PCT/US2011/047234 Dec. 22, 2011.
(Continued)

*Primary Examiner* — Michael Kahelin
(74) *Attorney, Agent, or Firm* — Wiley Rein LLP (57) ABSTRACT

A method of identifying potential driver sites for cardiac arrhythmias includes acquiring a plurality of electrograms from a plurality of locations on at least a portion of a patient's heart. Using the acquired electrograms, at least one electrical activity map is generated. Desirable electrical activity maps include complex fractionated electrogram standard deviation and mean maps, dominant frequency maps, peak-to-peak voltage maps, and activation sequence maps. Using one or more of these maps (e.g., by analyzing one or more electrogram morphological characteristics represented by these maps), at least one potential driver site can be detected.

18 Claims, 9 Drawing Sheets
(5 of 9 Drawing Sheet(s) Filed in Color)

(56) References Cited

U.S. PATENT DOCUMENTS

| | | | |
|---|---|---|---|
| 7,783,352 | B1 | 8/2010 | Ryu et al. |
| 8,478,393 | B2 * | 7/2013 | Ramanathan et al. ........ 600/523 |
| 2002/0151808 | A1 | 10/2002 | Schwartzman et al. |
| 2007/0055167 | A1 | 3/2007 | Bullinga |
| 2007/0073179 | A1 | 3/2007 | Afonso et al. |
| 2007/0197929 | A1 | 8/2007 | Porath et al. |
| 2007/0208260 | A1 | 9/2007 | Afonso |
| 2008/0009758 | A1 | 1/2008 | Voth |
| 2008/0114258 | A1 | 5/2008 | Zhang et al. |
| 2009/0192393 | A1 | 7/2009 | Hayam et al. |
| 2010/0004550 | A1 | 1/2010 | Ishay et al. |
| 2010/0094274 | A1 | 4/2010 | Narayan et al. |
| 2010/0152801 | A1 | 6/2010 | Koh et al. |

OTHER PUBLICATIONS

Sterns, L. et al., "Regional Capture of Human Atrial Fibrillation by Atrial Pacing at Map-Guided Sites", *The Canadian Journal of Cardiology*, vol. 24, Supplement E 2008.

Supplementary European Search Report issued in EP Patent Application No. 11831110.9 (Feb. 14, 2014).

Caldwell, Jane et al., "Ablation of complex fractionated atrial electrograms in catheter ablation for AF; where have we been and where are we going?", Current Cardiology Reviews, vol. 4, pp. 347-353, Nov. 2012.

Schuessler, RB et al., "Simultaneous epicardial and endocardial activation sequence mapping in the isolated canine right atrium", Circulation Journal of the American Heart Association, vol. 88, pp. 250-263, Jul. 1, 1993.

\* cited by examiner

METHOD AND SYSTEM FOR IDENTIFYING CARDIAC ARRHYTHMIA DRIVER SITES

CROSS-REFERENCE TO RELATED APPLICATIONS

This application is a continuation of U.S. application Ser. No. 12/923,769, filed 7 Oct. 2010, now U.S. Pat. No. 8,340, 766, issued 25 Dec. 2012, which is hereby incorporated by reference as though fully set forth herein.

BACKGROUND OF THE INVENTION

1. Field of the Invention

The instant invention relates to the treatment of cardiac arrhythmias, such as atrial fibrillation. In particular, the instant invention relates to the use of electrophysiological data in order to identify potential arrhythmic driver sites so as to facilitate the termination of the arrhythmia via the application of pacing.

2. Background Art

The mechanisms of AF in patients are not well understood. For a long time, it was believed that AF in patients was due to random propagation of multiple reentrant wavelets throughout the atria. A recent intraoperative mapping study from Waldo's group suggested that left atrial (LA) sources are of importance in patients with chronic AF.

Current therapeutic interventions for AF include various pharmacological therapies, ablative, and surgical techniques. These techniques not only demonstrate variable efficacy in treating paroxysmal and/or persistent AF, they are also subject to potential adverse effects.

Recently, several experimental and clinical studies, including those by Jalife's group, Schilling's group, Waldo's group, and St. Jude Medical CRM Research, have suggested that pace-termination of AF is possible in certain circumstances, particularly where the AF is due to a regular and stable activity that drives the rest of the atria in fibrillatory conduction. See, e.g., Goldstein RN et al., "Reliable Pace Termination of Atrial Fibrillation is Possible," *Circulation* 2003; 108 (Supp. IV):708; Verma A et al., "Regional Capture of Human Atrial Fibrillation by Atrial Pacing at Map-Guided Sites," *Europace* 2008; 10(1):49. Prior efforts at pace-termination, however, have not been routinely successful, for example because the pacing protocol applied was inappropriate and/or not properly located.

BRIEF SUMMARY OF THE INVENTION

It is therefore desirable to identify sites with regular activation (e.g., constant electrogram cycle length and morphology). Sites that exhibit these characteristics are likely arrhythmic driver sites, or are sufficiently close to such sites to follow their activation in a 1:1 manner. Thus, by identifying sites with regular activation, potential arrhythmic driver sites, and therefore potential sites for intelligent application of pacing in order to pace-terminate cardiac arrhythmias, are identified.

It is also desirable to prioritize potential arrhythmic driver sites for application of pacing.

It is another object of the present invention to determine appropriate pacing protocols to apply at one or more identified arrhythmic driver sites.

Disclosed herein is a method of identifying potential driver sites for cardiac arrhythmias, including the steps of: acquiring a plurality of electrograms from a plurality of locations on at least a portion of a patient's heart; generating at least one electrical activity map of the at least a portion of the patient's heart from the plurality of electrograms; and detecting at least one potential driver site based on at least one electrogram morphological characteristic represented by the at least one electrical activity map. The at least one electrical activity map is selected from the group consisting of: a complex fractionated electrogram standard deviation map; a complex fractionated electrogram mean map; a dominant frequency map; a peak-to-peak voltage map; and an activation sequence map. A graphical representation of the at least one electrical activity map may be displayed with the detected at least one potential driver site identified thereon.

The step of detecting at least one potential driver site based on at least one electrogram morphological characteristic represented by the at least one electrical activity map may include detecting at least one site having at least one electrogram morphological characteristic represented by the at least one electrical activity map that is indicative of driver activity. The at least one electrogram morphological characteristic represented by the at least one electrical activity map that is indicative of driver activity may be selected from the group consisting of: a cycle length between about 90 ms and about 200 ms; a cycle length variation of about 15 ms; a dominant frequency between about 5 Hz and about 10 Hz; presence of an isoelectric line; presence of a complex potential, multi-component; a peak-to-peak amplitude greater than about 1 mV; a slew rate between about 0.25 mv/s and about 1 mV/s; and an electrogram width of between about 15 ms and about 25 ms.

In some embodiments of the invention, at least two electrical activity maps of the at least a portion of the patient's heart will be generated from the plurality of electrograms. In other embodiments of the invention, a complex fractionated electrogram standard deviation map, a complex fractionated electrogram mean map, a dominant frequency map, and a peak-to-peak voltage map of the at least a portion of the patient's heart will all be generated. In embodiments where two or more electrical activity maps are generated, the step of detecting at least one potential driver site based on at least one electrogram morphological characteristic represented by the at least one electrical activity map may include detecting at least one site that exhibits at least one driver electrogram morphological characteristic in all generated electrical activity maps.

In another aspect, the present invention provides a method of identifying a target site for treatment of cardiac arrhythmia by pacing. The method includes the following steps: generating at least one electrical activity map of at least a portion of a patient's heart, wherein the at least one electrical activity map is selected from the group consisting of a complex fractionated electrogram standard deviation map; a complex fractionated electrogram mean map; a dominant frequency map; and a peak-to-peak voltage map; detecting one or more sites in the at least one electrical activity map exhibiting one or more electrogram morphological characteristics indicative of arrhythmic driver activity; and displaying a graphical representation of the at least one electrical activity map with the one or more detected sites identified as target sites thereon.

Typically, the step of detecting one or more sites in the at least one electrical activity map exhibiting one or more electrogram morphological characteristics indicative of arrhythmic driver activity includes: for each generated electrical activity map, detecting one or more sites exhibiting one or more electrogram morphological characteristics indicative of arrhythmic driver activity; and identifying as potential driver sites any detected sites exhibiting one or more electrogram morphological characteristics indicative of arrhythmic driver activity in all generated electrical activity maps.

It is also contemplated to assign a pacing priority to each of the detected sites based upon each detected site's electrogram cycle length variation, with higher treatment priorities being assigned to detected sites with lower electrogram cycle length variations.

Further, the one or more electrogram morphological characteristics indicative of arrhythmic driver activity may include a constant electrogram cycle length and a constant electrogram morphology.

Also disclosed herein is a method of treating cardiac arrhythmias by pacing, including the steps of: electrically mapping at least a portion of a patient's heart; identifying one or more driver sites on the at least a portion of a patient's heart based upon electrogram morphological characteristics represented by one or more electrical activity maps selected from the group consisting of a complex fractionated electrogram standard deviation map of the at least a portion of the patient's heart; a complex fractionated electrogram mean map of the at least a portion of the patient's heart; a dominant frequency map of the at least a portion of the patient's heart; and a peak-to-peak voltage map of the at least a portion of the patient's heart; and applying pacing to at least one of the identified one or more driver sites.

Optionally, a graphical representation of the one or more electrical activity maps may be displayed with the identified one or more driver sites represented thereon.

In some embodiments of the invention, the step of identifying one or more driver sites includes identifying one or more driver sites that exhibit one or more electrogram morphological characteristics indicative of driver activity in each of the one or more electrical activity maps. In other embodiments of the invention, the step of identifying one or more driver sites includes identifying one or more driver sites that exhibit one or more electrogram morphological characteristics indicative of driver activity in all of the one or more electrical activity maps.

The present invention also provides a system for identifying potential driver sites for cardiac arrhythmias, including: a mapping system to electrically map at least a portion of a patient's heart; a driver analysis processor that detects one or more potential driver sites on the at least a portion of a patient's heart based upon electrogram morphological characteristics represented by one or more electrical activity maps selected from the group consisting of a complex fractionated electrogram standard deviation map of the at least a portion of the patient's heart; a complex fractionated electrogram mean map of the at least a portion of the patient's heart; a dominant frequency map of the at least a portion of the patient's heart; a peak-to-peak voltage map of the at least a portion of the patient's heart; and an activation sequence map of the at least a portion of the patient's heart; and a display to present a graphical representation of the at least a portion of the patient's heart with the one or more detected potential driver sites identified thereon. Preferably, the mapping system is an electrical-field based localization system.

The system may optionally further include a pacing analysis processor that prioritizes the one or more detected potential driver sites for application of pacing and that determines an appropriate pacing protocol for at least some of the one or more detected potential driver sites and/or an electrogram characterization processor that characterizes locations on the at least a portion of the patient's heart as one of a driver location, a fractionated/polymorphic location, and a bystander location based on at least one electrogram morphological characteristic represented by the at least one electrical activity map.

An advantage of the present invention is that it analyzes maps of the electrical activity in a patient's heart in order to automatically identify likely driver sites for cardiac arrhythmias, including AF, such that pacing can be applied in the proper location.

Another advantage of the present invention is that it prioritizes the identified driver sites for application of pacing.

Yet another advantage of the present invention is that it facilitates the development of appropriate pacing protocols to terminate cardiac arrhythmias.

The foregoing and other aspects, features, details, utilities, and advantages of the present invention will be apparent from reading the following description and claims, and from reviewing the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 4a through 4e illustrate desirable electrical activity maps that may be utilized in connection with the methods disclosed herein, wherein:

DETAILED DESCRIPTION OF THE INVENTION

The present invention provides a method and system for identifying potential driver sites for cardiac arrhythmias from various maps of the electrical activity in a patient's heart, and thus for identifying likely sites where pacing can be applied to terminate the arrhythmia. For purposes of illustration, the invention will be described in detail in the context of treating AF. As discussed in further detail below, potential AF driver sites are those that exhibit regular activation (e.g., constant electrogram cycle length and morphology). It is contemplated, however, that the present invention may be practiced to good advantage in other contexts, such as for treatment of ventricular fibrillation, ventricular tachycardia, atrial flutter, and/or atrial tachycardia.

The invention will also be described with reference to a localization system, particularly the EnSite NavX™ navigation and visualization system of St. Jude Medical, Atrial Fibrillation Division, Inc., which utilizes an electrical field to localize a medical device within a patient's body. In addition to anatomical mapping (e.g., generating a geometric model of the patient's heart), the EnSite NavX™ system is capable of measuring the electrical activity of the patient's heart in order to generate the electrical activity maps ("EAMs") that are utilized in the methods disclosed herein. It should be understood, however, that the EAMs need not be generated by the localization system; indeed, it is within the scope of the invention for the EAMs to be generated in any fashion, such as by body surface mapping and mapping using a catheter such as the EnSite Array™ multi-electrode diagnostic catheter of St. Jude Medical, Atrial Fibrillation Division, Inc. One of ordinary skill in the art will generally appreciate the ways in which the various EAMs referred to herein may be generated. Likewise, other localization systems, such as the CARTO navigation and location system of Biosense Webster, Inc., the AURORA® system of Northern Digital Inc., or Sterotaxis' NIOBE® Magnetic Navigation System, may also be used in connection with the present invention.

Figure 1:
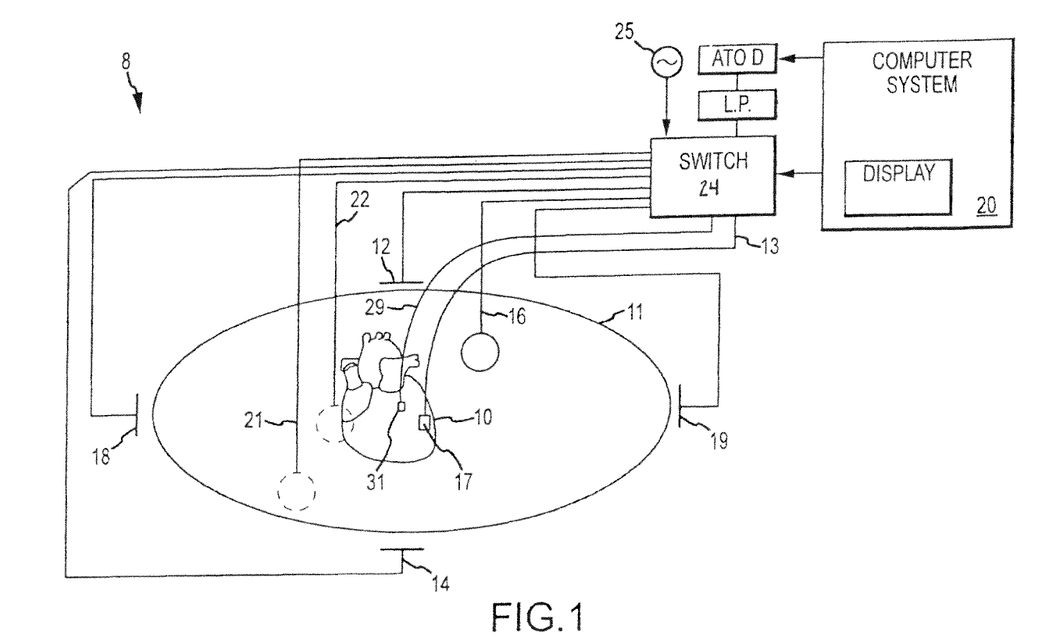
FIG. 1 is a schematic diagram of a localization system utilized in an electrophysiology study.

FIG. 1 shows a schematic diagram of a localization system 8 for conducting cardiac electrophysiology studies by navigating a cardiac catheter and measuring electrical activity occurring in a heart 10 of a patient 11 and three-dimensionally mapping the electrical activity and/or information related to or representative of the electrical activity so measured. System 8 can be used, for example, to create an anatomical model of the patient's heart 10 using one or more electrodes. As one of ordinary skill in the art will recognize, and as will be further described below, localization system 8 determines the location of objects, typically within a three-dimensional space, and expresses those locations as position information determined relative to at least one reference. System 8 can also be used to measure electrophysiology data at a plurality of points along a cardiac surface, and store the measured data in association with location information for each measurement point at which the electrophysiology data was measured, for example to create one or more EAMs of the patient's heart 10.

For simplicity of illustration, the patient 11 is depicted schematically as an oval. In the embodiment shown in FIG. 1, three sets of surface electrodes (e.g., patch electrodes) are shown applied to a surface of the patient 11, defining three generally orthogonal axes, referred to herein as an x-axis, a y-axis, and a z-axis. In other embodiments the electrodes could be positioned in other arrangements, for example multiple electrodes on a particular body surface. Likewise, the electrodes do not need to be on the body surface, but could be fixed on an external apparatus, or electrodes positioned internally to the body could be used.

In FIG. 1, the x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along a second axis generally orthogonal to the x-axis, such as along the inner thigh and neck regions of the patient, and may be referred to as the Left Leg and Neck electrodes. The z-axis electrodes 16, 22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intracardiac electrode 31, described in further detail below. It should also be appreciated that, in addition, the patient 11 may have most or all of the conventional electrocardiogram ("ECG" or "EKG") system leads in place. This ECG information is available to the system 8, although not illustrated in FIG. 1.

A representative catheter 13 having at least one electrode 17 (e.g., a distal electrode) is also shown. This representative catheter electrode 17 is referred to as the "roving electrode," "moving electrode," "measurement electrode," or "position measurement sensor" throughout this specification. Typically, multiple electrodes on catheter 13, or on multiple such catheters, will be used. In one embodiment, for example, localization system 8 may comprise sixty-four electrodes on twelve catheters disposed within the heart and/or vasculature of the patient. Of course, this embodiment is merely exemplary, and any number of electrodes and catheters may be used within the scope of the present invention.

Figure 2:
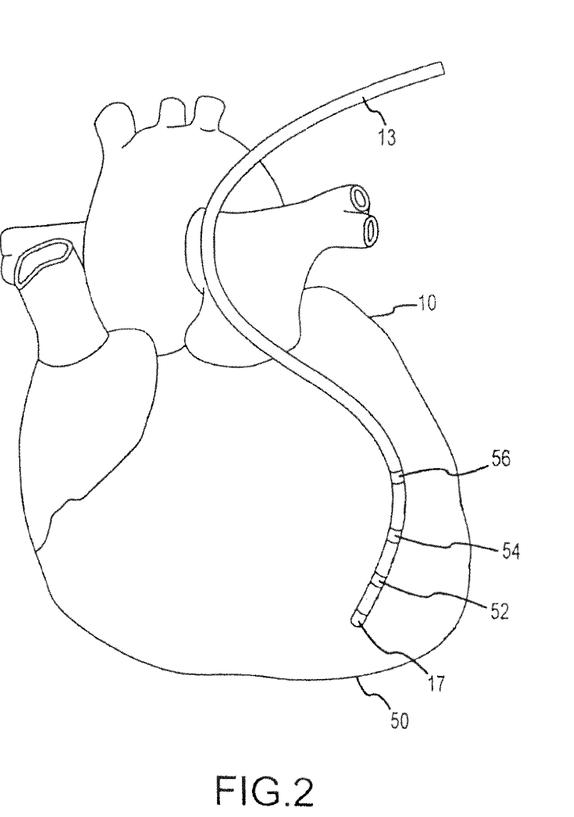
FIG. 2 depicts an exemplary catheter used in an electrophysiology study.

For purposes of this disclosure, an exemplary catheter 13 is shown in FIG. 2. In FIG. 2, catheter 13 extends into the left ventricle 50 of the patient's heart 10. Catheter 13 includes electrode 17 on its distal tip, as well as a plurality of additional position measurement sensors (e.g., measurement electrodes) 52, 54, 56 spaced along its length. Typically, the spacing between adjacent electrodes will be known, though it should be understood that the electrodes may not be evenly spaced along catheter 13 or of equal size to each other. Since each of these electrodes 17, 52, 54, 56 lies within the patient, location data may be collected simultaneously for each of the electrodes by localization system 8. Thus, each position measurement sensor (e.g., electrodes 17, 52, 54, 56) may generate a localization signal that describes the position, and optionally also the orientation, of catheter 13 within the localization field generated by patch electrodes 12/14, 18/19, and 16/22.

Returning now to FIG. 1, an optional fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrodes (e.g., electrodes 17, 52, 54, 56), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system for the localization field.

Each surface electrode is coupled to the multiplex switch 24, and the pairs of surface electrodes are selected by software running on a computer 20, which couples the surface electrodes to a signal generator 25. The computer 20, for example, may comprise a conventional general-purpose computer, a special-purpose computer, a distributed computer, or any other type of computer. The computer 20 may comprise one or more processors, such as a single central processing unit ("CPU"), or a plurality of processing units, commonly referred to as a parallel processing environment, which may execute instructions to practice the various aspects of the present invention described herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Likewise, the electrodes 12, 14, 18, 19, 16, and 22 (or any number of electrodes) could be positioned in any other effective arrangement for driving a current to or sensing a current from an electrode in the heart. For example, multiple electrodes could be placed on the back, sides, and/or belly of patient 11. Additionally, such non-orthogonal methodologies add to the flexibility of the system.

For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The roving electrodes 17, 52, 54, 56 placed in the heart 10 are exposed to the field from a current pulse and are measured with respect to ground, such as belly patch 21. In practice the catheters within the heart may contain more or fewer electrodes than the four shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which localization system 8 measures positions. Data sets from each of the surface electrodes, the internal electrodes, and the virtual electrodes may all be used to determine the location of the roving electrodes 17, 52, 54, 56 within heart 10.

The measured voltages may be used to determine the location in three-dimensional space of the electrodes inside the heart, such as roving electrodes 17, 52, 54, 56, relative to a reference location, such as reference electrode 31. That is, the voltages measured at reference electrode 31 may be used to define the origin of a coordinate system, while the voltages measured at roving electrodes 17, 52, 54, 56 may be used to express the location of roving electrodes 17, 52, 54, 56 relative to the origin. For purposes of this disclosure, the invention will be described in connection with a three-dimensional (x, y, z) Cartesian coordinate system. It should be understood, however, that other coordinate systems, such as spherical and cylindrical coordinate systems in three dimensions and polar coordinate systems in two dimensions, are within the scope of the invention.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described in U.S. Pat. No. 7,263,397, which is hereby incorporated herein by reference in its entirety. The electrode data may also be used to compensate for changes in the impedance of the body of the patient as described in co-pending U.S. application Ser. No. 11/227,580, filed 15 Sep. 2005, which is also incorporated herein by reference in its entirety.

In summary, the system 8 first selects a set of surface electrodes and then drives them with current pulses. While the current pulses are being delivered, electrical activity, such as the voltages measured at least one of the remaining surface electrodes and in vivo electrodes, is measured and stored. Compensation for artifacts, such as respiration and/or impedance shifting, may be performed as indicated above.

In a preferred embodiment, the localization/mapping system is the EnSite NavX™ navigation and visualization system of St. Jude Medical, Atrial Fibrillation Division, Inc., which generates the electrical fields described above. Other localization systems, however, may be used in connection with the present invention, including for example, the CARTO navigation and location system of Biosense Webster, Inc., the AURORA® system of Northern Digital Inc., or Sterotaxis' NIOBE® Magnetic Navigation System, all of which utilize magnetic fields rather than electrical fields. The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

The fields generated by localization system 8, whether an electrical field (e.g., EnSite NavX™), a magnetic field (e.g., CARTO, AURORA®, NIOBE®), or another suitable field, may be referred to generically as "localization fields," while the elements generating the fields, such as surface electrodes 12, 14, 16, 18, 19, and 22 may be generically referred to as "localization field generators." As described above, surface electrodes 12, 14, 16, 18, 19, and 22 may also function as detectors to measure the characteristics of the localization field (e.g., the voltages measured at roving electrodes 17, 52, 54, 56, or a current from roving electrodes 17, 52, 54, 56), and thus may also be referred to as "localization elements." Though the present invention will be described primarily in the context of a localization system that generates an electrical field, one of ordinary skill in the art will understand how to apply the principles disclosed herein in other types of localization fields, and in particular other types of non-ionizing localization fields (e.g., by replacing electrodes 17, 52, 54, 56 with coils to detect different components of a magnetic field).

Figure 3:
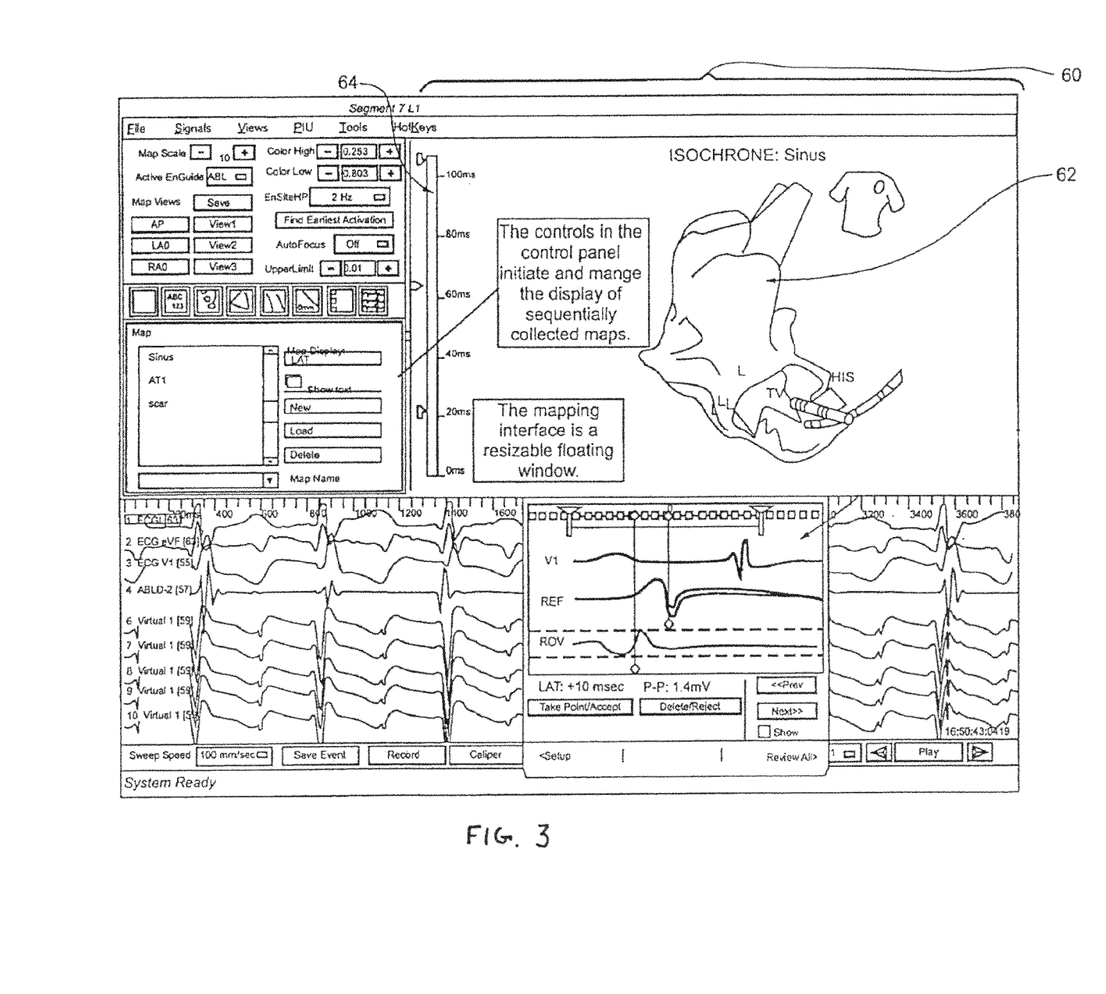
FIG. 3 is an illustrative graphical representation of an activation sequence map, including an anatomical map of the patient's heart with electrophysiology data overlaid thereon.

Various electrophysiology data (e.g., electrograms from a plurality of locations on at least a portion of a patient's heart) may be measured (e.g., using electrodes 17, 52, 54, 56), and may optionally be presented graphically to a cardiologist through the display 23 of the system 8 shown in FIG. 1. The display 23 may be used to show data to a user, such as a physician, and to present certain options that allow the user to tailor the configuration of the system 8 for a particular use. FIG. 3 is an illustrative display. For example, an image panel 60 may show a three dimensional anatomical model of a heart chamber 62 identifying regions that received a depolarization waveform at the same time (i.e., "isochrones") mapped to the anatomical model in false color or grayscale. The isochrones are, in one variation, mapped to three dimensional coordinates (e.g., (x, y, z)) corresponding to the electrogram from which they were obtained. The isochrones may also be shown in guide bar 64 as a key, identifying information associated with a particular color or grayscale mapped to the three dimensional model. In this image, the locations of multiple electrodes on a pair of catheters are also mapped to the three dimensional anatomical model. Other data that may be mapped to the heart surface model include, for example, the magnitude of a measured voltage and the timing relationship of a signal with respect to heartbeat events. Further, the peak-to-peak voltage measured at a particular location on the heart wall may be mapped to show areas of diminished conductivity and may reflect an infarct region of the heart. It should be noted that the contents on the display can be easily modified and the specific data discussed herein is illustrative only and not limiting of the invention.

The graphical representation of an activation sequence map superimposed on an anatomical model of a patient's heart as depicted in image panel 60 of FIG. 3 is one example of a graphical representation of an EAM. Of course, EAMs may be graphically represented in different fashions without departing from the spirit and scope of the present invention.

For purposes of the present invention, desirable EAMs include, without limitation and in order of descending preference: (1) complex fractionated electrogram standard deviation maps; (2) complex fractionated electrogram mean maps; (3) dominant frequency maps; (4) peak-to-peak voltage maps; and (5) activation sequence maps. As discussed above, the EnSite NavX™ system is capable of generating each of these EAMs, and can therefore be employed to good advantage in the present invention, as it permits near-simultaneous anatomical and electrical mapping of the patient's heart. FIGS. 4a through 4e are illustrative examples of these desirable EAMs.

One or more of the EAMs described above may then be utilized to detect one or more potential driver sites for cardiac arrhythmias, such as AF. In particular, one or more of the EAMs may be analyzed to detect electrogram morphological characteristics ("EMCs") that are indicative of AF driver activity at one or more sites on the patient's heart. The EMCs analyzed may be those actually measured at particular locations on the patient's heart. Alternatively, or in addition, EMCs may be derived from such measurements and assigned to other locations where no measurements were actually taken. For example, EMC values at non-measured locations may be extrapolated from neighboring measured EMC values, such as disclosed in U.S. application Ser. No. 11/647,276, which is expressly incorporated by reference as though fully set forth herein.

Figure 5:
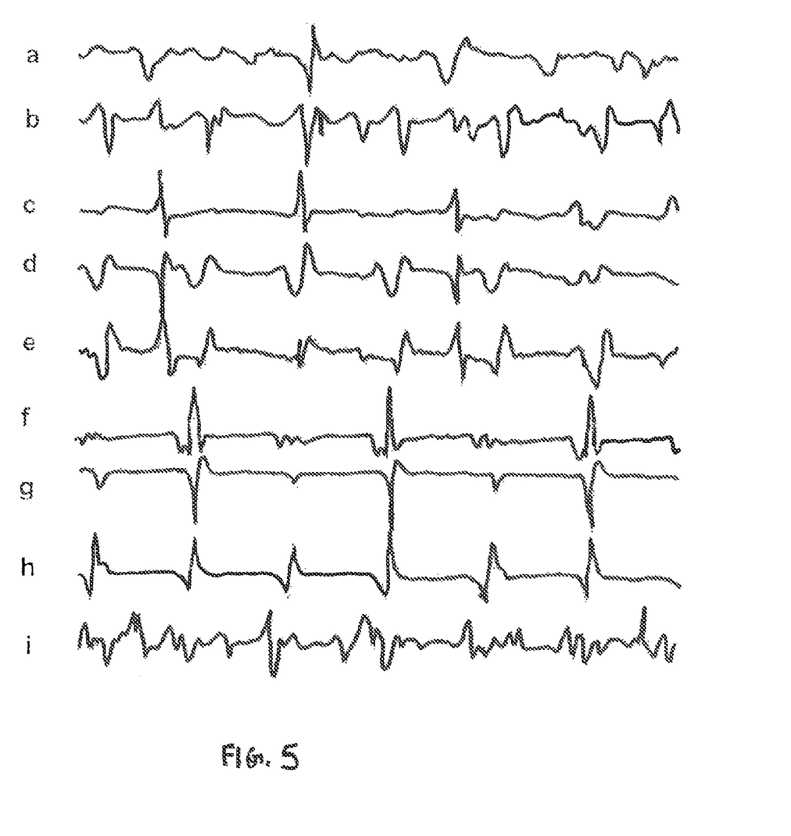
FIG. 5 are representative electrograms taken at nine different sites within a patient's heart depicting sites having regular activation (e.g., driver characteristics), fractionation/polymorphism, and bystander activity.

For purposes of the present invention, EMCs useful in detecting AF driver activity include, without limitation and in order of descending preference: (1) cycle lengths; (2) cycle length variations; (3) dominant frequencies; (4) isoelectric line; (5) complex potential, multicomponent; (6) peak-to-peak amplitudes; (7) slew rates; and (8) electrogram widths. Specific values of these EMCs indicative of AF driver activity, as well as of fractionated/polymorphic and bystander activity, are shown in Table 1. FIG. 5 illustrates the various types of electrograms described in Table 1.

TABLE 1

Discrimination of Electrograms By EMCs

| EMC | Driver Activity | Fractionated/ Polymorphic | Bystander |
| --- | --- | --- | --- |
| Cycle Length (ms) | 90-200 | 30-120 | Above 120 |
| Cycle Length Variation (ms) | 15 | Above 15 | Large |
| Dominant Frequency (Hz) | 5-10 | 8-33 | Below 8 |
| Isoelectric Line | Must Have | Not Present | Must Have |
| Complex Potential, Multicomponent | Could Have | Continuous Fractionation | Present |
| Peak-to-Peak Amplitude (mV) | Above 1 | Below 1 | Above 1 |
| Slew Rate (mV/s) | 0.25-1 | Catheter Dependent | N/A |
| Exemplary Electrogram(s) in FIG. 5 | Site h | Sites a, b, and i | Sites d and g |

One of ordinary skill in the art will appreciate that each of the EAMs described above will represent different EMCs (that is, not all EMCs will be visible on all EAMs; the EMCs represented will vary between EAMs). Thus, it should be understood from this disclosure that the effectiveness of the methods disclosed herein in detecting AF driver sites may be improved by utilizing additional EAMs, typically selected according to the order of preference described above, thereby allowing the analysis of a greater number of EMCs, again typically selected according to the order of preference described above, for indications of AF driver activity.

Accordingly, in some embodiments of the invention, at least two EAMs are generated from the acquired electrograms and analyzed for one or more EMCs indicative of AF driver activity, while in other embodiments of the invention, at least three EAMs are generated from the acquired electrograms and analyzed for one or more EMCs indicative of AF driver activity. In still other embodiments of the invention, the acquired electrograms are used to generate each of a complex fractionated electrogram standard deviation map, a complex fractionated electrogram mean map, a dominant frequency map, and a peak-to-peak voltage map, with each of these four maps being analyzed for one or more EMCs indicative of AF driver activity.

Figure 4A:
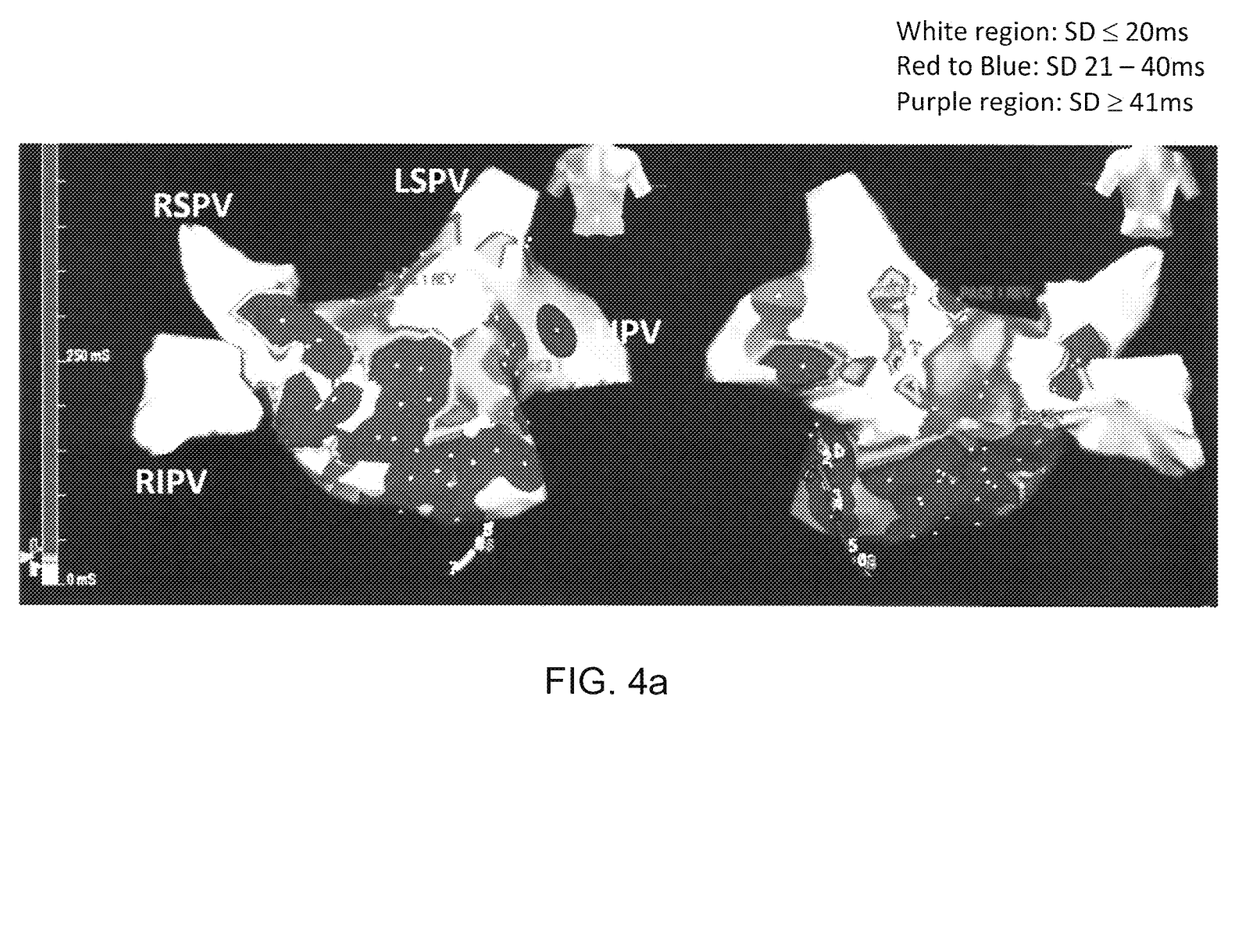
FIG. 4a is an illustrative complex fractionated electrogram standard deviation map.
Figure 4B:
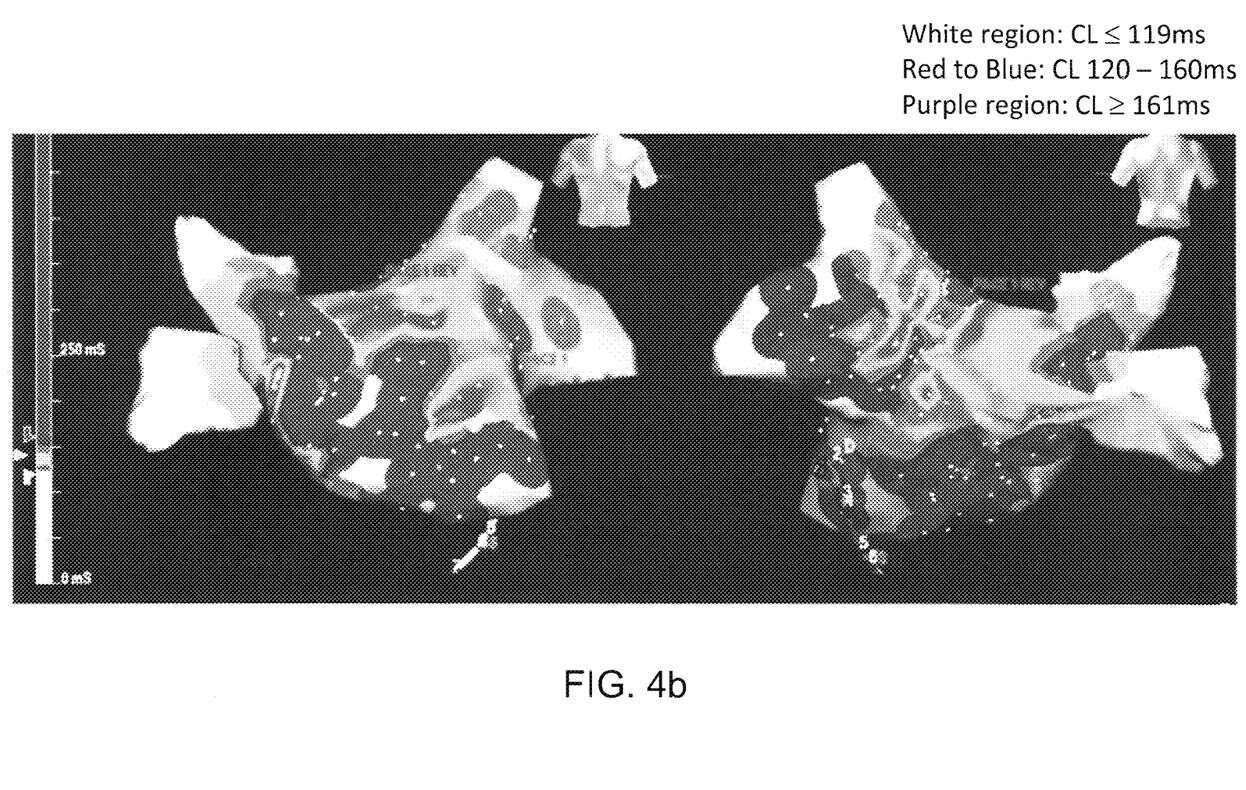
FIG. 4b is an illustrative complex fractionated electrogram mean map.
Figure 4C:
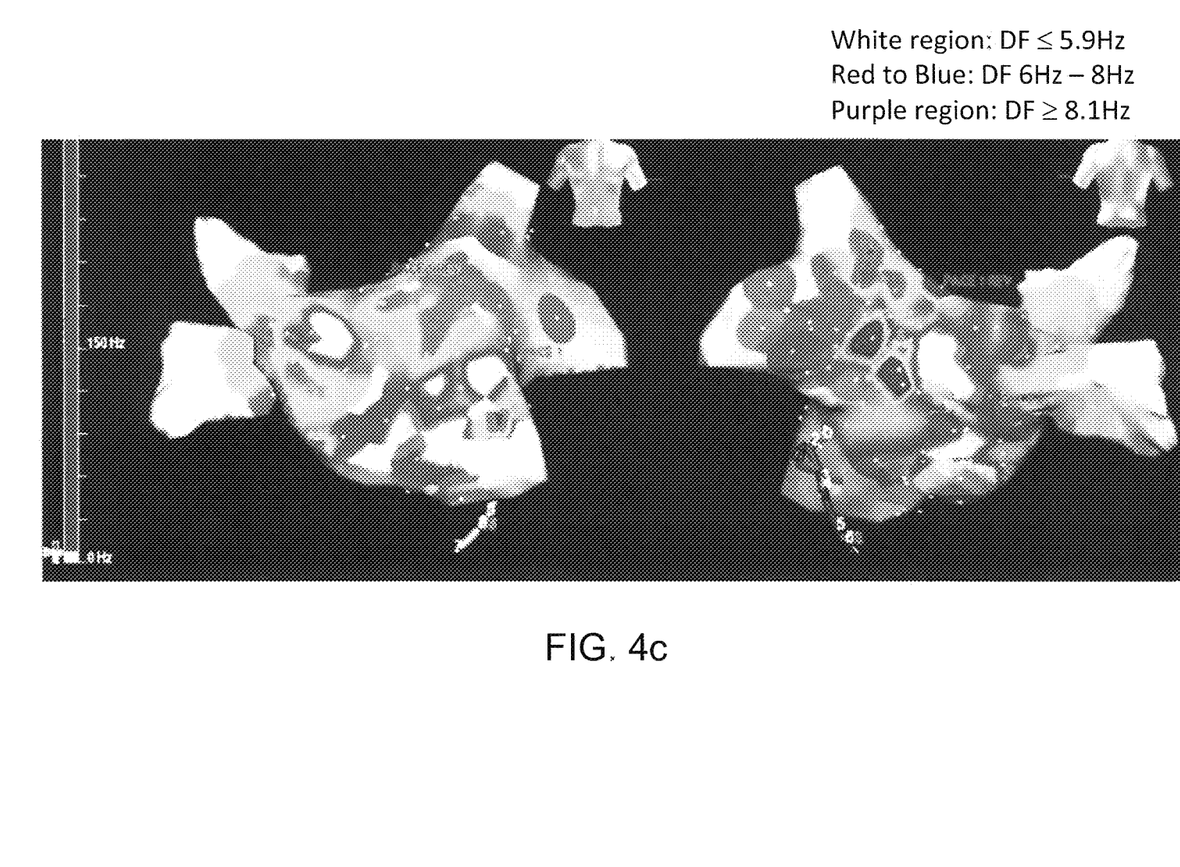
FIG. 4c is an illustrative dominant frequency map.
Figure 4D:
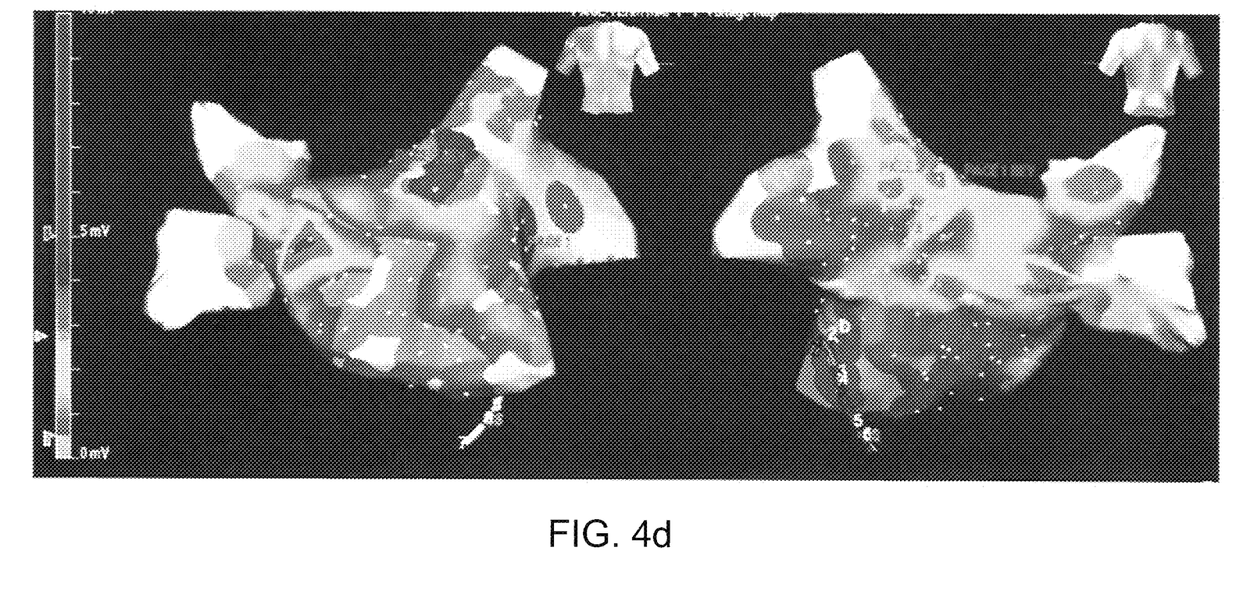
FIG. 4d is an illustrative peak-to-peak voltage map.
Figure 4E:
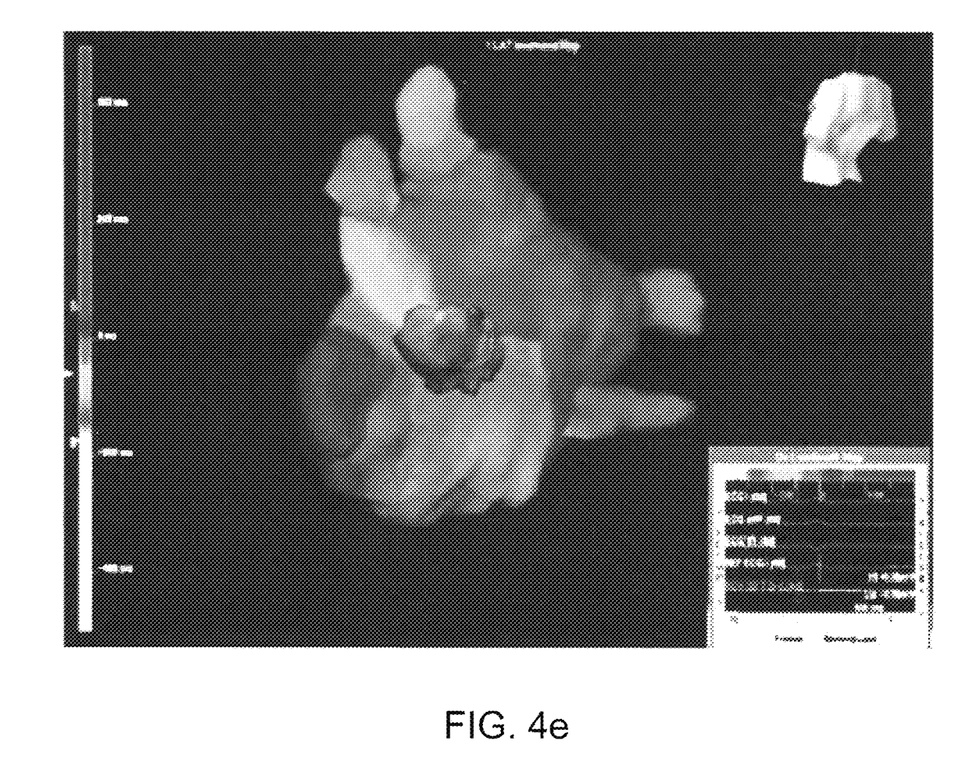
FIG. 4e is an illustrative activation sequence map.

For purposes of illustrating how AF driver sites can be identified based on EMCs in a particular EAM, FIG. 4a is an exemplary cycle length variation map. The white regions in FIG. 4a identify areas where the cycle length variation is less than 20 ms, and which are therefore potential AF driver sites consistent with the values shown in Table 1. The red to blue regions identify areas where the cycle length variation is between 21 ms and 40 ms, while the purple regions identify areas where the cycle length variation is greater than or equal to 41 ms.

Regardless of the number of EAMs generated, potential AF driver sites are, as discussed above, identified based on EMCs at those sites. Typically, potential AF driver sites are identified as those sites that exhibit at least one EMC indicative of AF driver activity in each and every generated EAM. For example, where only a complex fractionated electrogram mean map and a peak-to-peak voltage map are used, a site that exhibits a cycle length indicative of driver activity in the complex fractionated electrogram mean map and a peak-to-peak voltage indicative of driver activity in the peak-to-peak voltage map may be identified as a potential AF driver site, and thus may be targeted for pacing.

Graphically, it is contemplated that two or more EAMs may be overlaid upon each other in order to facilitate identifying potential AF driver sites. It is also contemplated to overlay the EAMs upon an anatomical model of the patient's heart, such as shown in FIG. 3, in order to provide the practitioner with an indication of where these potential AF driver sites are relative to the patient's anatomy.

Further, the graphical representations may be annotated in some fashion (e.g., a flag, blinking dot, or other suitable icon) to indicate the location of the identified potential AF driver sites. The graphical representations may also be annotated to specify EMC values at various locations, in particular at the identified potential AF driver sites.

As discussed above, the EnSite NavX™ system is a particularly desirable localization system for use in connection with the present invention. This is, in part, due to the flexibility of the EnSite NavX™ system to generate and display various EAMs with settings that facilitate the identification of potential AF driver sites thereon. For purposes of illustration, Tables 2 and 3 provide suggested display variable settings when using the EnSite NavX™ system to generate and display complex fractionated electrogram standard deviation, complex fractionated electrogram mean, and dominant frequency maps for use with the present teachings.

TABLE 2

Suggested Settings for CFE-Std Dev and CFE-Mean Maps

| | |
| --- | --- |
| Low V_ID | 0.5 mV |
| P-P | 0.5 mV |
| Width | 20 ms |
| Refractory | 90 ms |
| Segment Length | 4 s |
| Interior Projection | 4 mm |
| Exterior Projection | 4 mm |
| Interpolation | 6 mm |

TABLE 3

Suggested Settings for Dominant Frequency Map

Enable "Rectify"

| Low Frequency | 4 Hz |
|---|---|
| High Frequency | 15 Hz |

For the complex fractionated electrogram standard deviation map (color high 50 ms-color low 20 ms), it is also desirable to disable the toggle "show" where there were no detections in the electrogram. This will enable identification of potential AF driver electrograms that may have been overlooked due to a too-high P-P setting, in which case the P-P threshold may be lowered.

For the complex fractionated electrogram mean map (color high 250 ms-color low 100 ms), it is desirable to note those areas on the map where a low complex fractionated electrogram standard deviation also had a low complex fractionated electrogram mean cycle length.

For the dominant frequency map (color high 7 Hz-color low 4 Hz), it is desirable to confirm that the frequency is the reciprocal of the cycle length at the sites of interest.

Table 4 provides values for various parameters used in the pacing site selection protocol described above. These parameters are listed in order of descending preference.

TABLE 4

Values for Pacing Site Selection Protocol Parameters

| Segment Length | 2-8 s |
|---|---|
| Cycle Length Variation | 20 ms |
| | More preferably 15 ms |
| | Most preferably 20 ms |
| Refractory | 80-150 ms |
| Width | 15-25 ms |
| Rectify | Enabled (dominant frequency map only) |
| P-P sensitivity | 0.3-2 mV |
| Low VID | 0.3-1 mV |

Once potential AF driver sites are identified, pacing can be applied to one or more of those sites in an effort to terminate the AF. In some embodiments of the invention, pacing sites are prioritized based on cycle length variation, with higher priority belonging to sites with lower electrogram cycle length variations. Suitable pacing protocols may be selected based at least in part upon one or more of a dominant frequency value and a complex fractionated electrogram mean value at each site where pacing is applied, for example as described in U.S. application Ser. Nos. 11/473,403 and 11/473,715, both filed 23 Jun. 2006, and both incorporated by reference as though fully set forth herein.

The methods of detecting and identifying potential AF driver sites described above are preferably executed automatically. They may be executed by one or more computer systems (e.g., computer system 20), and may be software implemented (e.g., one or more software programs executed by one or more computer systems or processors), hardware implemented (e.g., a series of instructions stored in one or more solid state devices), or a combination of both. The computer may be a conventional general purpose computer, a special purpose computer, a distributed computer, or any other type of computer. Further, the computer may comprise one or more processors, such as a single central processing unit or a plurality of processing units, commonly referred to as a parallel processing environment. The term "processor" as used herein refers to a computer microprocessor and/or a software program (e.g., a software module or separate program) that is designed to be executed by one or more microprocessors running on one or more computer systems.

Although several embodiments of this invention have been described above with a certain degree of particularity, those skilled in the art could make numerous alterations to the disclosed embodiments without departing from the spirit or scope of this invention. For example, it is within the spirit and scope of the present invention to identify as potential AF driver sites points on the patient's heart that exhibit AF driver EMCs in some EAMs, but do not exhibit AF driver EMCs in other EAMs (though, typically, at least one potential AF driver site will be identified in each EAM, even if the identified sites differ from EAM-to-EAM). It is also contemplated that, in certain embodiments of the invention, the methods herein may be used to characterize non-driver locations (e.g., fractionated/polymorphic or bystander) based on EMCs.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of identifying driver sites for cardiac arrhythmias, comprising:

acquiring a plurality of electrograms reflecting electrical activity occurring on at least a portion of a patient's heart;

generating at least one electrical activity map from the plurality of electrograms, wherein the at least one electrical activity map represents at least one electrogram morphological characteristic;

displaying a graphical representation of the at least one electrical activity map using a first display convention to depict the at least one electrogram morphological characteristic represented in the at least one electrical activity map;

analyzing, using at least one processor, the at least one electrical activity map to identify at least one site for application of pacing on the at least a portion of the patient's heart, wherein the at least one electrogram morphological characteristic at the identified at least one site for application of pacing is indicative of driver activity; and annotating a location of the identified at least one site for application of pacing on the graphical representation of the at least one electrical activity map using a second display convention, wherein the at least one electrogram morphological characteristic at the identified at least one site for application of pacing comprises regular electrogram activity, and wherein the regular electrogram activity comprises a constant electrogram cycle length and a constant electrogram morphology.

2. The method according to claim 1, wherein the electrogram morphological characteristic represented in the at least one electrical activity map is selected from the group consisting of:
- a cycle length between about 90 ms and about 200 ms;
- a cycle length variation of about 15 ms;
- a dominant frequency between about 5 Hz and about 10 Hz;
- presence of an isoelectric line;
- presence of a complex potential, multicomponent;
- a peak-to-peak amplitude greater than about 1 mV;
- a slew rate between about 0.25 mv/s and about 1 mV/s; and
- an electrogram width of between about 15 ms and about 25 ms.

3. The method according to claim 1, wherein the step of generating at least one electrical activity map comprises generating at least two electrical activity maps.

4. The method according to claim 3, wherein the step of analyzing the at least one electrical activity map to identify at least one site for application of pacing comprises identifying at least one site that exhibits at least one electrogram morphological characteristic indicative of driver activity in each generated electrical activity map.

5. The method according to claim 1, wherein the step of acquiring a plurality of electrograms comprises acquiring the plurality of electrograms via a body surface mapping process.

6. The method according to claim 1, wherein the step of acquiring plurality of electrograms comprises acquiring the plurality of electrograms via a non-contact mapping process.

7. The method according to claim 1, further comprising assigning a pacing priority to each identified site for application of pacing.

8. The method according to claim 1, wherein the first display convention comprises at least one of color scale and greyscale.

9. The method according to claim 1, wherein the second display convention comprises iconography.

10. A system for identifying driver sites for cardiac arrhythmias, comprising:
- a mapping system configured to electrically map at least a portion of a patient's heart;
- a driver analysis processor configured to identify one or more pacing sites on the at least a portion of the patient's heart by analyzing at least one electrical activity map for one or more sites on the patient's heart that exhibit at least one electrogram morphological characteristic indicative of driver activity,
- wherein the at least one electrogram morphological characteristic at the identified one or more pacing sites comprises regular electrogram activity, and wherein the regular electrogram activity comprises a constant electrogram cycle length and a constant electrogram morphology; and
- a display configured to present a graphical representation of the at least a portion of the patient's heart with the at least one electrogram morphological characteristic depicted thereon using a first display convention and locations of the one or more identified pacing sites annotated thereon using a second display convention.

11. The system according to claim 10, wherein the mapping system comprises an electrical-field based localization system.

12. The system according to claim 10, wherein the mapping system comprises a non-contact mapping electrophysiology catheter.

13. The system according to claim 10, further comprising a pacing analysis processor that prioritizes the one or more identified pacing sites for application of pacing and that determines an appropriate pacing protocol for at least some of the one or more identified pacing sites.

14. The system according to claim 10, further comprising an electrogram characterization processor that characterizes locations on the at least a portion of the patient's heart as one of a driver location, a fractionated/polymorphic location, and a bystander location according to at least one electrogram morphological characteristic at each respective location on the at least a portion of the patient's heart as represented in the at least one electrical activity map.

15. A controller for identifying driver sites for cardiac arrhythmias, comprising:
- a first processor, wherein the processor is configured to:
  - receive as input a plurality of electrograms reflecting electrical activity occurring on at least a portion of a patient's heart;
  - detect at least one electrogram morphological characteristic indicative of arrhythmic driver activity within the plurality of electrograms, wherein the at least one electrogram morphological characteristic comprises regular electrogram activity, wherein the regular electrogram activity comprises a constant electrogram cycle length and a constant electrogram morphology; and
  - output an identification of at least one pacing location on the at least a portion of the patient's heart, wherein the at least one pacing location corresponds to at least one location on the at least a portion of the patient's heart where the at least one electrogram morphological characteristic indicative of arrhythmic driver activity was detected, wherein the output comprises a graphical representation of the at least a portion of the patient's heart with the at least one electrogram morphological characteristic depicted thereon using a first display convention and the identification of the at least one pacing location annotated thereon using a second display convention.

16. The controller according to claim 15, further comprising a second processor configured to prioritize identified pacing locations for application of pacing and that determines an appropriate pacing protocol for at least some of the identified pacing locations.

17. The controller according to claim 15, further comprising a third processor configured to characterize locations on the at least a portion of the patient's heart as one of a driver location, a fractionated/polymorphic location, and a bystander location according to at least one electrogram morphological characteristic detected at each respective location.

18. The controller according to claim 15, wherein the first processor is configured to receive inputs from a non-contact mapping electrophysiology catheter.

* * * * *